United States Patent
Wilson Moya et al.

(10) Patent No.: US 10,634,682 B2
(45) Date of Patent: Apr. 28, 2020

(54) METHOD FOR VISUALIZING BIOMOLECULES, SUCH AS PROTEINS OR NUCLEIC ACIDS, WITH THE UNAIDED EYE, WITHOUT NEEDING TO USE POTENTIALLY TOXIC COMPOUNDS, EXPOSURE TO ULTRAVIOLET (UV) LIGHT OR FLUORESCENCE

(71) Applicant: UNIVERSIDAD DE CHILE, Santiago (CL)

(72) Inventors: Christian Andres Marcelo Wilson Moya, Santiago (CL); Jorge Babul Cattan, Santiago (CL); Gabriela Isabel Contreras Arriagada, Santiago (CL)

(73) Assignee: UNIVERSIDAD DE CHILE, Santiago (CL)

(*) Notice: Subject to any disclaimer, the term of this patent is extended or adjusted under 35 U.S.C. 154(b) by 399 days.

(21) Appl. No.: 15/524,788

(22) PCT Filed: Oct. 29, 2015

(86) PCT No.: PCT/IB2015/058363
§ 371 (c)(1),
(2) Date: May 5, 2017

(87) PCT Pub. No.: WO2016/071809
PCT Pub. Date: May 12, 2016

(65) Prior Publication Data
US 2017/0356919 A1 Dec. 14, 2017

(30) Foreign Application Priority Data
Nov. 5, 2014 (CL) .................................. 2014-3000

(51) Int. Cl.
*G01N 33/68* (2006.01)
*G01N 1/30* (2006.01)
*G01N 33/52* (2006.01)
*C09B 23/04* (2006.01)
*C12Q 1/68* (2018.01)
*G01N 27/447* (2006.01)
*G06T 7/00* (2017.01)
*G01N 21/64* (2006.01)

(52) U.S. Cl.
CPC ......... *G01N 33/6803* (2013.01); *C09B 23/04* (2013.01); *C12Q 1/68* (2013.01);
(Continued)

(58) Field of Classification Search
CPC .... G01N 1/30; G01N 33/52; G01N 27/44726; G01N 2021/6439
See application file for complete search history.

(56) References Cited

PUBLICATIONS

Whiteley, et al. "Analysis of microbial functional diversity within water-stressed soil communities by flow cytometric analysis and CTC+ cell sorting", Journal of Microbiological Methods, 54(2): p. 257-267, Aug. 2003.*
(Continued)

*Primary Examiner* — J. Christopher Ball
(74) *Attorney, Agent, or Firm* — Lucas & Mercanti, LLP

(57) ABSTRACT

The present invention relates to a method of visualizing biomolecules, having the steps of: a) providing a sample of immobilized biomolecules in a matrix and carry on the electrophoresis process; b) incubating the matrix of step a) in a solution containing a cyanine-derived molecule, for a time of 5 to 60 minutes, at room temperature, in a container preventing exposure to light, shaking the container at less of 75 rpm; c) transferring the matrix from step b) to a container with a solution having: at least one tetrazolium salt and incubating for a time of 15 to 120 minutes at room temperature under light exposure; d) removing the matrix with immobilized biomolecules from the previous step and washing with distilled water; and e) visualizing directly by the naked eye the biomolecules immobilized in the matrix.

13 Claims, 1 Drawing Sheet

(52) U.S. Cl.
CPC .............. *G01N 1/30* (2013.01); *G01N 27/447* (2013.01); *G01N 33/52* (2013.01); *G06T 7/0012* (2013.01); *G01N 27/44726* (2013.01); *G01N 2021/6439* (2013.01); *G06T 2207/30242* (2013.01)

(56) References Cited

PUBLICATIONS

L.R. Williams; Staining nucleic acids and proteins in electrophoresis gels; Biotechnic & Histochemistry; 2001; 76(3); pp. 127-132.
J. Williams, et al; Improved nitro blue tetrazolium staining of creatine kinase isoenzymes following agarose gel electrophoresis or isoelectric . . . ; Electrophoresis; 1987; vol. 8; pp. 536-537.
K.S. Sri Venugopal, et al; Artifactual staining of proteins on polyacrylamide gels by nitrobluetetrazolium chloride and phenazine methosulfate; Analytical Biochemistry; 1980; vol. 101(1); 1 page.
I. Johnson, et al; The molecular probes handbook: a guide to fluorescent probes and labeling technologies; 11th edition; 2010; chapters 8 and 9.
A.J. Paredes, et al; Development of a novel and simple visible staining method for inexpensive DNA detection and quantification; XXXVIII Reunion Anual Sociedad de Bioquimica y Biologia Molecular de Chile; Sep. 2015, Abstract Book, Poster.
International Search Report dated Feb. 3, 2016 for PCT/IB2015/058363.

\* cited by examiner

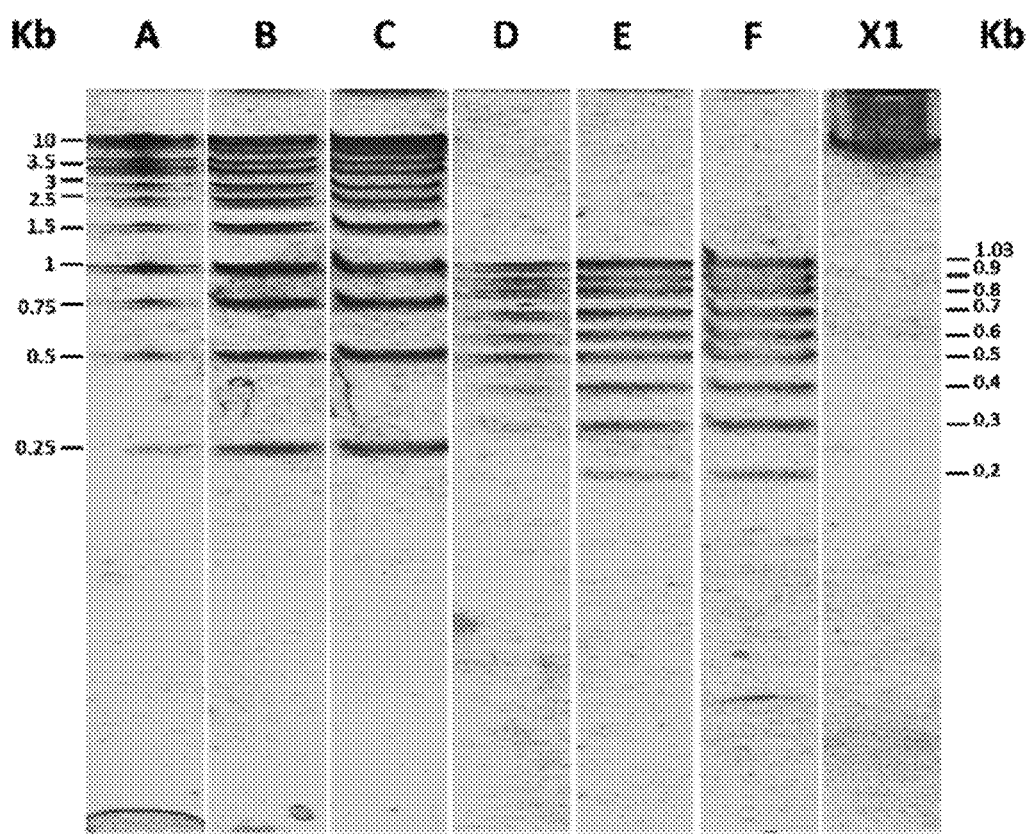

METHOD FOR VISUALIZING BIOMOLECULES, SUCH AS PROTEINS OR NUCLEIC ACIDS, WITH THE UNAIDED EYE, WITHOUT NEEDING TO USE POTENTIALLY TOXIC COMPOUNDS, EXPOSURE TO ULTRAVIOLET (UV) LIGHT OR FLUORESCENCE

CROSS REFERENCE TO RELATED APPLICATION

This Application is a 371 of PCT/IB2015/058363 filed on Oct. 29, 2015, which claims priority of Chilean Application No. 2014-3000 filed Nov. 5, 2014, both of which are incorporated herein by reference.

The present invention describes a simple and direct method for visualizing nucleic acids and proteins by the naked eye without the need to use compounds with potential toxic effects for health, exposure to ultraviolet (UV) light or by fluorescence for their visualization.

STATE OF THE ART

The process for detecting biomolecules such as proteins and nucleic acids is essential in biological research, clinical diagnosis and industrial analysis services. These methods are frequently and routinely used in scientific research and basic analysis in many laboratories. In scientific research, in order to carry on experiments and analyzes it is necessary visualization and quantification of DNA and proteins on a daily basis, currently exist some classic techniques to do so which require specialized instruments.

There is also an important use of this type of methods in the industry, particularly in the wine industry, for example, wherein yeasts are required for fermentation and the diverse microbiological composition determines wine quality (Cocolin L, Rantsiou K, L Iacumin L, Zironi R, Comi G. (2004) Molecular detection and identification of Brettanomyces/Dekkera bruxellensis and Brettanomyces/Dekkera anomalus in spoiled wines Appl. Environ. Microb. 70(3): 1347-1355). For these reasons, the determination of the organisms contained in the wine is necessary. In addition, there are pathogenic microorganisms that attack the vineyard and cause millionaires losses in this crop. In order to quickly detect these microorganisms molecular strategies such as PCR are used (polymerase chain reaction). This methodology consists of amplifying a specific region of DNA from the organism under analyisis (Sambrook, J., Fritsch, AND. F., And Maniatis, T. (2001). Molecular Cloning. Ne w York: Cold spring harbor laboratory press. Vol. 2). This DNA fragment is visualized by a gel. If the reaction is positive, i.e., when the organism is found in the sample, the DNA will appear as a band in the gel and this band is generally observed through ultraviolet light (UV) or fluorescence (Sambrook et al. 2001).

This same DNA visualization strategy is also employed in clinical analysis for the determination of pathogens and also in molecular analysis and research laboratories. Techniques such as PCR and DNA restriction analysis, RAPD (Random Amplified Polymorphic DNA), RFLP (Restriction Fragment Length Polymorfism), AFLP (Amplified Fragment Length Polymorphism), Cloning, Southern blot, among others, are the most used for pathogen detection.

The most widely used method for the separation and subsequent visualization of nucleic acids and proteins is gel electrophoresis. In this method, for example, the nucleic acid sample is deposited onto a gel wherein an electric field is applied enabling the molecules to migrate according to its size. Further, nucleic acids, and particularly DNA, are associated with intercalating agents, such as ethidium bromide, SYBR® Green (cyanine dye), among others. These intercalating agents change their radiation emission when binding to DNA, in answer to exposure to UV light or through fluorescence. Therefore, DNA visualization requires equipment capable of emitting at a specific radiation. In addition, to photograph DNA a camera associated with a platform that protects the user from radiation and isolates the camera from external light is needed.

The present invention describes a method for visualizing nucleic acids and proteins without the need to exposure to UV light or through fluorescence, i.e., DNA can be directly observed. This allows better handling and savings on equipment, space and steps associated with the visualization process.

Currently, there are various ways of visualizing nucleic acids without the need to expose them to UV light, for example, by using a silver nitrate-based compound, brilliant cresyl blue, crystal violet and Nile blue, eosin Y, ethyl violet, and thionine. These strategies are very little used since they are not specific for DNA, since they also detect proteins and other biomolecules such as lipoproteins. On the other hand, silver nitrate produce a long lasting stain on the surface on which is exposed, therefore is difficult to handle, dangerous if not handled properly and DNA cannot be recovered after staining.

There are no methods today for observing with the naked eye and distinguish DNA and protein in the same gel, which makes some studies difficult, such as simultaneous detection of both biomolecules. Protein-DNA interaction studies are essential in biochemistry research, e.g., for detecting some protein specific binding sites to DNA zones through molecule crosslinking studies, whereby the silver nitrate-based staining method is not suitable for these applications because the nonspecificity thereof.

In summary, there is no method for visualizing biomolecules that is simple, cheaper, sensitive, and specific for each biomolecule based on a general principle of detection that does not require additional instruments. The present invention will make possible to bring this type of analysis to isolated places which have less resources and lack the necessary equipment, where users would not need extensive training, new laboratories or large investments, and new laboratories could be created in areas where previously was not possible (isolated areas, low-income areas, etc.). In addition, if there are natural catastrophes in isolated areas, they may have access to analytical laboratories that can quantify and visualize biological molecules, such as nucleic acids and proteins.

U.S. Pat. No. 6,887,668, by example, discloses a method for the separation and detection of nucleic acids contained in a sample by electrophoresis. The detection step is performed using detection by Laser Induced Fluorescence (LIF) or UV detection at 254 nm.

(Williams, 2001 Williams LR (2001) Staining Nucleic Acids And Proteins In Electrophores is Gels. Biotech. Histochem. 76:127-32), describes different methods for detecting nucleic acids in electrophoresis gels. It details the use of ethidium bromide, SYBR® Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine), SYBR® Green II (RNA cyanine dye), SYBR® Gold (unsymmetrical cyanine dye), GELSTAR® (fluorescent nucleic acid gel stain), RADIANT RED® (fluorescent dye for staining nucleic acids) and berberine with mordan yellow 3R. These staining systems are detected by fluorescence or by UV radiation. Staining methods based on the use of methylene blue, Nile blue and silver nitrate are also described None of the documents found describe the combinations or results obtained in the present invention.

SUMMARY OF THE INVENTION

The present invention describes a method for visualizing biomolecules by the naked eye, such as proteins or nucleic acids, without the need to use potentially toxic compounds. The visualization is done directly, without using UV light or by means of fluorescence. This method is based on the binding of a specific molecule to each biomolecule, which is capable of the reduction of tetrazolium salt to form formazan.

DESCRIPTION OF THE FIGURES

FIG. 1: Polyacrylamide Gel visualized without exposure to UV light. Lanes A-B correspond to the DNA molecular weight standard, 1 KB (Fermentas) at 100 ng (A), 500 ng (B), 1000 ng (C), and MASSRULER™ (quantification and sizing of DNA fragments dye) standard (Fermentas) at 60.8 ng (D), 3044 ng (E), 608 ng (F). Lane X1 corresponds to a phage lambda DNA sample of unknown concentration. Molecular weight standard sizes are shown: 1 KB and MASSRULER™ (quantification and sizing of DNA fragments dye), at the right and left, respectively.

DESCRIPTION OF THE INVENTION

The present invention describes a method of visualizing biomolecules. The method is generally based on the use of an intercalating molecule that binds the biomolecule; this molecule must have the capacity of reduction of tetrazolium salt for its subsequent transformation into formazan and precipitation of this compound, since the formazan is colored this allow a direct visualization, In particular, the method of the present invention is preferably applied to biomolecules immobilized in a matrix. The visualization method comprises the following steps:
a) providing a biomolecule sample immobilized in a matrix and carry on the electrophoresis process;
b) incubating the matrix of step a) in a solution containing one cyanine-derived molecule for a time of 2 to 90 minutes, at room temperature (25° C.), in a container without exposure to light, shaking the container at less than 75 rpm. The solution with the cyanine-derived molecule may optionally contain up to 15% v/v acetic acid;
c) transferring the matrix from step b) to a container with a solution comprising: at least a tetrazolium salt and incubating for a time between 5 and 120 minutes, at room temperature, under light exposure;
d) removing the matrix with immobilized molecules from the previous step and washing to remove traces of tetrazolium salt to avoid over-exposure or over-development;
e) visualizing by the naked eye the biomolecules immobilized in the matrix in the form of bands.

The method further includes a step after step e) consisting in the quantification of the biomolecule visualized in the matrix, comprising the steps of:
(i) taking a photograph of the gel;
(ii) quantifying pixels of each visualized band;
(iii) making a calibration curve correlating the band intensity, number of pixels, with the amount of added DNA; and
(iv) quantifying the added DNA using the calibration curve of step (iii) from the number of pixels obtained on each band in step (ii), for quantifying the biomolecule visualized in the matrix.

The method may additionally include a step after step b) consisting on washing the matrix with the biomolecules immobilized therein with a solution of acetic acid at a concentration of 1% to 15% v/v.

In a particular embodiment of the invention, the biomolecules are nucleic acids, more specifically, single stranded or double stranded DNA or RNA molecules; proteins or polypeptides.

The matrix on which the method of the presented invention is applied may be a gel, such as a polyacrylamide gel, an agarose gel, a starch gel, a cellulose matrix, a nitrocellulose matrix, a polyvinyl difluoride membrane, etc.

The cyanine-derived molecule corresponds to a cyanine pigment, such as a molecule selected from the group consisting of Cy2, Cy3, Cy3B, Cy3.5, Cy5, Cy5.5, Cy7, phthalocyanine, merocyanine, indocyanine, anthocyanin, or molecules derived therefrom, which are used at a final concentration of between 0.1 and 10 µM.

The cyanine-derived molecule corresponds to a cyanine pigment, such as a molecule selected from the group consisting of:

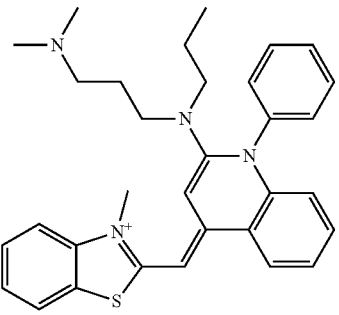

Formula I

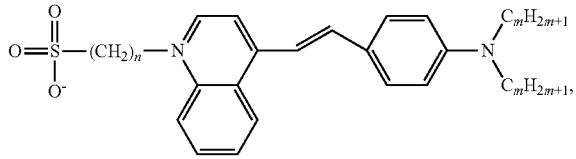

Formula II wherein m may be 5 or 6, and
n may be 2, 3 or 4;

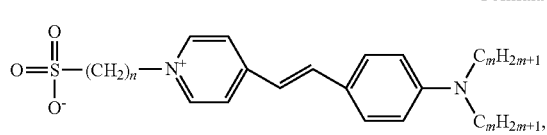

Formula III wherein m may be 2, 3, 4, 5, 6, 7, 8, 9 or 10, and
n may be 3 or 4;

Formula IV

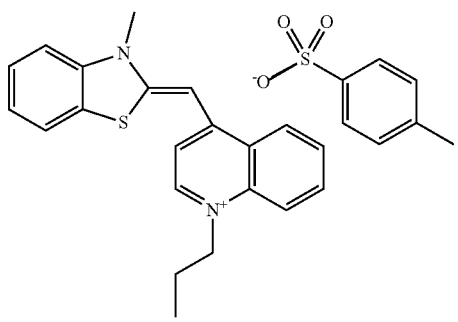

including commercial versions thereof, such as SYBR® green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine), SYPRO® red (protein gel stain), SYPRO® orange (protein gel stain), SYBR® safe ((Z)-4-((3-Methylbenzo[d]thiazol-2(3H)-ylidene)methyl)-1-propylquinolin-1-ium 4-methylbenzenesulfonate), or molecules derived therefrom, which are used at a final concentration of between 0.1 and 10 µM.

The cyanine-derived molecule may also correspond to a molecule derived from cyanine, such as a molecule selected from the group consisting of commercial versions of SYBR® green II (RNA cyanine dye) and SYBR® Gold (unsymmetrical cyanine dye), which are used at a final concentration of between 0.1 and 10 µM.

Notwithstanding the above, the skilled artisan can further considering other cyanine-derived molecules suitable for carrying out the method of the presented invention, and the above list is not limiting.

In another embodiment, the tetrazolium salt is selected from the group consisting of INT (2-(4-iodophenyl)-3-(4-nitrophenyl)-5-phenyl-2H-tetrazolium) chloride); MTT (3-(4,5-dimethyl-2-thiazolyl)-2,5-diphenyl-2H-tetrazolium bromide); XTT (2,3-bis-(2-methoxy-4-nitro-5-sulfophenyl)-2H-tetrazolium-5-carboxanilide); MTS (3-(4,5-dimethylthiazol-2-yl)-5-(3-carboxymethoxyphenyl)-2-(4-5-sulfophenyl)-2H-tetrazolium); TTC or tetrazolium chloride (2,3,5-triphenyl-2H-tetrazolium chloride); NBT (nitro blue tetrazolium chloride), which are used at a concentration of 0.1 to 1 mM.

In a particular embodiment, the method additionally includes a step after step ii) which consists in washing the matrix with the biomolecules immobilized with a solution of acetic acid at a concentration of 1% to 15% v/v.

The present invention has wide application in various fields, both in biological sciences research, clinical diagnosis and industrial service analysis.

EXAMPLES OF APPLICATION

Example 1 a) For separating DNA, this molecule was placed together with a loading solution (0.25% bromophenol blue, 0.25% xylene cyanol and 30% glycerol). This solution was then placed in an agarose matrix in a solution containing 1×TAE buffer (40 mM Tris, 20 mM acetate and 1 mM EDTA). By applying a voltage difference to the gel, the DNA migrates to the positive pole and DNA molecules are separated as they pass through the matrix according to their different sizes.

b) The matrix was then placed in a container with cyanine-derived DNA intercalating molecule SYBR® Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine) at a concentration of 1.96 µM (INVITROGEN®, diluted 10,000 fold, i.e., 1× final dilution) the gel completely covered in 1×TAE buffer for approx. 30 min. The container containing the gel was protected from light by covering with an aluminum foil. The gel was put under shaking at less than 50 rpm and at room temperature for 30 min.

c) The gel was placed in a container containing 0.198 mM Nitro blue Tetrazolium Chloride (NBT) for at least 15 min in the presence of natural light (not covered with aluminum foil).

d) The gel was removed from this solution and the NBT residues were removed with distilled water to avoid over-exposure.

e) DNA bands were visualized by the naked eye and without the need to exposure to UV light or using fluorescence equipment FIG. 1 shows an example wherein the polyacrylamide gel was loaded with two DNA molecular weight markers, i.e. DNA fragments of known size and concentration: 1 KB (Fermentas®, SM0313) and MASSRULER™ (quantification and sizing of DNA fragments dye) (Fermentas®, SM0383), whose DNA sizes are 10 to 0.25 Kb and 1031 to 80 bp, respectively. Both standards were added at different concentrations, 1 KB at 100 ng, 500 ng, 1000 ng, and MASSRULER™ (quantification and sizing of DNA fragments dye) at 60.8 ng; 3044 ng and 608 ng. After electrophoresis process, polyacrylamide gel was placed in a SYBR® Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine) solution and subsequently in 0.19 mM NBT solution for 90 min. Subsequently, the gel was photographed without exposure to UV light (FIG. 1). As shown in FIG. 1, the color intensity and area of each band are proportional to DNA concentration. An image processing program was used to quantify the size and concentration of a sample of interest. From the DNA bands the total area of each marker was related to the concentration. From this relationship was obtained an equation that allowed to calculate the concentration of a DNA sample of unknown concentration, which was of 191 ng.

Band area is proportional to DNA concentration, as in the usual visualization methods. In addition, DNA is specifically visualized and proteins are not.

Example 2 a) For visualizing proteins, these molecules were placed onto a polyacrylamide matrix and the electrophoresis process was carried out.

b) The gel was placed in a container containing the intercalating agent SYPRO® red (protein gel stain) at a concentration of 3.92 µM (INVITROGEN®, 5000 fold dilution) and 7.5% (v/v) acetic acid. It was covered with aluminum foil to protect the intercalating agent from light. The gel was incubated for 30 min shaking at less than 50 rpm at room temperature.

c) The gel was removed and rinsed in 7.5% acetic acid to remove the excess of SYPRO® red (protein gel stain) from its surface and placed in 0.19 mM NBT for at least 90 min.

d) The gel was removed from this solution and the NBT residues were removed with distilled water.

e) Protein bands were visualized by the naked eye and without the need to exposure to UV light.

Example 3 a) For separating RNA, this molecule was placed together with a loading solution (0.25% bromophenol blue, 0.25% xylene cyanol and 15% ficoll). This solution was then placed onto a polyacrylamide matrix in a solution containing 1×TAE buffer (40 mM Tris, 20 mM acetate and 1 mM EDTA). By applying a voltage difference to the gel, the RNA migrates to the positive pole and RNA molecules are separated as they pass through the matrix according to their different sizes.
b) The matrix was then placed in a container with the cyanine-derived RNA intercalating molecule SYBR® Green II (RNA cyanine dye) at a concentration of 1.96 µM (INVITROGEN®, 10,000 fold dilution, i.e. 1× final dilution) the gel completely covered in 1×TAE buffer for approx. 30 min. The container containing the gel was protected from light by covering with an aluminum foil. It was put under shaking at less than 50 rpm and at room temperature for 30 min.
c) The gel was placed in a container containing 0.198 mM of Nitro blue Tetrazolium Chloride (NBT) for at least 15 min in the presence of natural light (not covered with aluminum foil).
d) The gel was removed from this solution and the NBT residues were removed with distilled water to avoid over-exposure.
e) RNA bands were visualized by the naked eye and without the need to exposure to UV light or using fluorescence equipment.

The invention claimed is:
1. A method of visualizing biomolecules, wherein it comprises the following steps:
   a) providing a sample of biomolecules immobilized in a matrix and carry on the electrophoresis process;
   b) incubating the matrix of step a) in a solution containing a cyanine-derived molecule, for a time of 5 to 60 minutes, at room temperature, in a container preventing light exposure, shaking the container at less than 75 rpm;
   c) transferring the matrix of step b) to a container with a solution comprising: at least one tetrazolium salt and incubating for a time of 15 to 120 minutes at room temperature under light exposure;
   d) removing the matrix with immobilized biomolecules from the previous step and washing with distilled water; and
   e) visualizing directly by the naked eye the biomolecules immobilized in the matrix.
2. The method of visualizing biomolecules according to claim 1, wherein it further comprises a step after step e) consisting of quantifying the biomolecule visualized in the matrix, comprising the steps of:
   (i) taking a photograph of the gel;
   (ii) quantifying pixels of each visualized band;
   (iii) making a calibration curve correlating the band intensity, number of pixels, with the amount of added DNA; and
   (iv) quantifying the added DNA using the calibration curve of step (iii) from the number of pixels obtained on each band in step (ii), for quantifying the biomolecule visualized in the matrix.
3. The method of visualizing biomolecules according to claim 1, wherein the biomolecules are nucleic acids.
4. The method of visualizing biomolecules according to claim 1, wherein the matrix on which the method of the present invention is selected from the group consisting of a polyacrylamide gel, an agarose gel, a starch gel, a cellulose matrix, a nitrocellulose matrix, and a polyvinyl difluoride membrane.
5. The method of visualizing biomolecules according to claim 1, wherein the solution with the cyanine-derived molecule further contains 7.5% acetic acid.
6. The method of visualizing biomolecules according to claim 1, wherein the cyanine-derived molecule corresponds to a cyanine pigment.
7. The method of visualizing biomolecules according to claim 1, wherein the cyanine-derived molecule is selected from the group consisting of Cy2, Cy3, Cy3B, Cy3.5, Cy5, Cy5.5, Cy7, phthalocyanine, merocyanine, indocyanine, anthocyanin, and molecules derived therefrom, which are used at a final concentration of between 0.1 and 10 µM.
8. The method of visualizing biomolecules according to claim 1, wherein the cyanine-derived molecule is selected from the group consisting of:

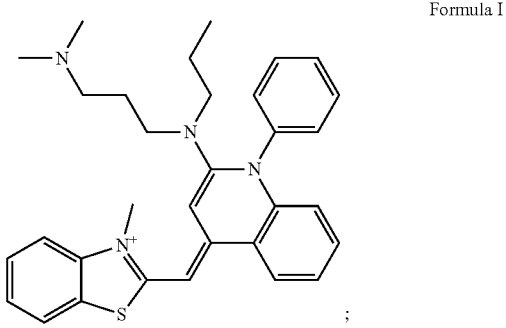

Formula I

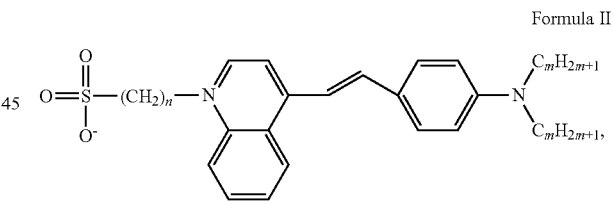

Formula II wherein m may be 5 or 6, and n may be 2, 3 or 4;

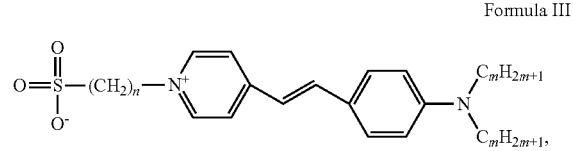

Formula III wherein m may be 2, 3, 4, 5, 6, 7, 8, 9 or 10, and n may be 3 or 4;

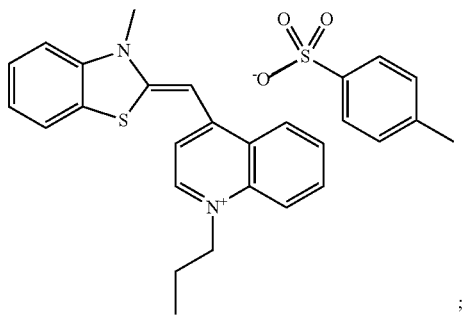

Formula IV and molecules derived therefrom, which are used at a final concentration of between 0.1 and 10 μM.

9. The method of visualizing biomolecules according to claim 1, wherein the cyanine-derived molecule is selected from the group consisting of RNA cyanine dye, asymmetrical cyanine dye, and unsymmetrical cyanine dye, which are used at a final concentration of between 0.1 and 10 μM.

10. The method of visualizing biomolecules according to claim 1, wherein the tetrazolium salt is selected from the group consisting of INT (2-(4-iodophenyl)-3-(4-nitrophenyl)-5-phenyl-2H-tetrazolium) chloride), MTT (3-(4,5-dimethyl-2-thiazolyl)-2,5-diphenyl-2H-tetrazolium bromide), XTT (2,3-bis-(2-methoxy-4-nitro-5-sulfophenyl)-2H-tetrazolium-5-carboxanilide), MTS (3-(4,5-dimethylthiazol-2-yl)-5-(3-carboxymethoxyphenyl)-2-(4-5-sulfophenyl)-2H-tetrazolium), TTC or tetrazolium chloride (2,3,5-triphenyl-2H-tetrazolium chloride), and NBT (nitro blue tetrazolium chloride), which are used at a concentration of between 0.1 to 1 mM.

11. The method of visualizing biomolecules according to claim 1, wherein the method further comprises a step after step (ii) which consists in washing the matrix with the biomolecules immobilized with a solution of acetic acid at a concentration of 1% to 15% v/v.

12. The method of visualizing biomolecules according to claim 1, wherein the biomolecules are single stranded or double stranded DNA or RNA molecules.

13. The method of visualizing biomolecules according to claim 1, wherein the biomolecules are protein or polypeptides.

* * * * *